United States Patent [19]

Windheuser

[11] 4,289,751

[45] Sep. 15, 1981

[54] EFFERVESCENT ENTERIC-COATED FORMULATION OF SOLUBLE FORM OF ERYTHROMYCIN AND THERAPEUTIC USE THEREOF

[75] Inventor: John J. Windheuser, Lawrence, Kans.

[73] Assignee: Merck & Co., Inc., Rahway, N.J.

[21] Appl. No.: 131,183

[22] Filed: Mar. 17, 1980

Related U.S. Application Data

[63] Continuation of Ser. No. 53,363, Jun. 29, 1979, abandoned.

[51] Int. Cl.³ .................. A61K 9/46; A61K 9/36; A61K 31/71
[52] U.S. Cl. .................................... 424/35; 424/44; 424/181
[58] Field of Search .................. 424/32, 33, 35, 44, 424/181

[56] References Cited

U.S. PATENT DOCUMENTS

| | | | |
|---|---|---|---|
| 2,798,024 | 7/1957 | Zapapas et al. | 424/35 |
| 2,801,952 | 8/1957 | Himelick | 424/181 |
| 2,830,982 | 4/1958 | Stainbrook et al. | 424/181 |
| 2,866,735 | 12/1958 | Himelick | 424/181 |
| 2,897,121 | 7/1959 | Wagner | 424/33 |
| 2,969,352 | 1/1961 | Ruskin | 424/181 |
| 2,993,833 | 7/1961 | Stephens | 424/181 |
| 3,081,233 | 3/1963 | Enz et al. | 424/35 |
| 3,131,123 | 4/1964 | Masquelier | 424/44 |
| 3,198,787 | 8/1965 | Hagemann et al. | 424/181 |
| 3,531,460 | 9/1970 | Ferrari et al. | 424/181 |
| 3,689,645 | 9/1972 | Sinkula | 424/181 |
| 3,843,787 | 10/1974 | Fabrizio | 424/181 |
| 3,865,935 | 2/1975 | Amann | 424/181 |
| 3,878,192 | 4/1975 | Blasina et al. | 424/181 |
| 3,891,755 | 6/1975 | Mehta | 424/181 |
| 3,961,041 | 6/1976 | Nishimura et al. | 424/44 |
| 4,013,820 | 3/1977 | Farhadieh et al. | 424/181 |
| 4,076,804 | 2/1978 | Singiser et al. | 424/181 |
| 4,147,768 | 4/1979 | Shaffer et al. | 424/35 |

FOREIGN PATENT DOCUMENTS

| | | | |
|---|---|---|---|
| 749864 | 10/1970 | Belgium | 424/44 |
| 754346 | 1/1971 | Belgium | 424/44 |
| 936803 | 11/1973 | Canada | 424/44 |

*Primary Examiner*—Shep K. Rose
*Attorney, Agent, or Firm*—Burns, Doane, Swecker & Mathis

[57] ABSTRACT

Improved delivery and absorption of erythromycin in warm-blooded animals is achieved by administering thereto a non-toxic pharmaceutical effervescent enteric-coated tablet comprising:

(a) an antibiotic effective amount of a non-toxic pharmaceutically acceptable soluble form of erythromycin;

(b) a non-toxic pharmaceutically acceptable inert diluent; and (c) a non-toxic pharmaceutically acceptable effervescent couple acid and base; and (d) a non-toxic pharmaceutically acceptable enteric coating maintained over the tableted mixture of (a), (b), and (c) above.

The subject composition is extremely useful in the treatment of bacterial infections in warm-blooded animals, particularly in the mitigation and treatment of upper and lower respiratory tract, skin and soft tissue infections of mild to moderate severity.

10 Claims, No Drawings

EFFERVESCENT ENTERIC-COATED FORMULATION OF SOLUBLE FORM OF ERYTHROMYCIN AND THERAPEUTIC USE THEREOF

This is a continuation, of application Ser. No. 53,363, filed June 29, 1979, now abandoned.

TECHNICAL FIELD OF THE INVENTION

The present invention is directed to a novel effervescent enteric-coated formulation containing a soluble form of erythromycin, capable of improved delivery and absorption of the drug in warm-blooded animals.

BACKGROUND OF THE PRIOR ART

Erythromycin is a broad spectrum macrolide antibiotic produced by a strain of *Streptomyces erythreus*. This drug has found wide usage in the mitigation and treatment of upper and lower respiratory tract, skin and soft tissue infections of mild to moderate severity. However, oral administration of the drug suffers from a major disadvantage, i.e., erythromycin is unstable in the acid medium found in the stomach. This instability results in erratic absorption of the drug because of changing gastric conditions which cause degradation of the drug to varying degrees depending on such factors as food intake, water volume, activity and emotional stress. As a result of these biological variations, the bioavailability of erythromycin can vary from as little as 20% to 50% absorption, even in the same patient. Generally, less than half the drug ingested is absorbed and available for antimicrobial activity.

Numerous attempts have been made in the past to overcome the problem of gastric degradation and enhance activity by modifying the erythromycin molecule or by modifying the dosage form of the drug. Thus, one approach has been to protect the erythromycin molecule by altering its physical-chemical characteristics, primarily by the preparation of insoluble derivatives such as erythromycin estolate, erythromycin cetyl sulfate, erythromycin propionate, erythromycin stearate and others. The rationale behind this approach has been that an insoluble derivative would be expected to traverse the stomach without significant degradation and then be available for absorption in the alkaline portion of the intestines. Although this approach has shown moderate success, the problem of instability has not been solved and serious bioavailability deficiencies remain.

The other prior art approach to the gastric degradation problem has involved protecting the drug from gastric fluids by preparing tablets of erythromycin which are treated in such a manner as to render them insoluble in the gastric fluids but subject to dissolution in the upper intestinal tract. Thus, a number of firms have prepared and marketed enteric-coated forms of erythromycin base, e.g., Upjohn's E-MYCIN ® tablets. The problem of acid instability has clearly been overcome by this approach, but, again, bioavailability problems remain.

It has been determined that the major approaches employed in the past have not been entirely satisfactory because the insoluble derivatives (e.g., the estolate and cetyl sulfate) and erythromycin base itself are in fact *highly* insoluble. Thus, these compounds, do not exhibit a high rate of dissolution and in fact dissolve only very slowly as the drug passes down the intestinal tract. This in itself would not be a problem except for the fact that it has been found that erythromycin is absorbed primarily from the duodenum (the first and shortest part of the small intestine, generally being about 10 inches in length), with little or no absorption occurring below this segment of the intestine.

SUMMARY OF THE INVENTION

In view of the foregoing, it is apparent that a serious need exists for an improved solid oral dosage form for administering erythromycin. Thus, it is an object of the present invention to provide a solid oral form of erythromycin which will be protected from gastric degradation but which will deliver to the intestine, rapidly and in a site-specific manner, a soluble form of the drug.

The foregoing object, resulting in the positive and reproducible delivery of erythromycin at the specific site where it is most readily absorbed, is achieved by orally administering to a warm-blooded animal a non-toxic pharmaceutical effervescent enteric-coated tablet comprising:

(a) an antibiotic effective amount of a non-toxic pharmaceutically acceptable solution form of erythromycin;

(b) a non-toxic pharmaceutically acceptable inert diluent;

(c) a non-toxic pharmaceutically acceptable effervescent couple acid and base; and (d) a non-toxic pharmaceutically acceptable enteric coating maintained over the tableted mixture of (a), (b), and (c) above.

The present invention thus provides a unique delivery system for erythromycin which protects the drug from the actions of the acidic gastric contents, allowing the dosage form to pass intact through the stomach, yet upon the slightest rupture of the coating due to the intestinal fluids, said system rapidly and completely delivers the drug from the dosage form in the duodenal region. This accomplishment of site specific delivery and rapid drug dissolution at the site of drug absorption allows more complete and more reproducible absorption of the drug and is in some cases expected to allow the use of smaller doses of the drug, which in turn could result in decreased side effects.

DETAILED DESCRIPTION OF THE INVENTION

The phrase "soluble form of erythromycin" as used herein includes any form through which erythromycin can be delivered as a soluble species. Such forms include soluble derivatives of erythromycin, for example, erythromycin lactobionate, erythromycin phosphate, erythromycin glucoheptonate, erythromycin gluconate and like soluble salts, which are typically derived from the antibiotic base by treatment with an appropriate acid. Reference is made to U.S. Pat. Nos. 2,761,859 and 2,852,429, expressly incorporated by reference herein and relied upon, for a description of typical soluble salts and processes for their preparation.

It would also be possible to employ as the soluble form of erythromycin, a specially formulated composition wherein erythromycin base or other ordinarily insoluble form of erythromycin has been rendered soluble by appropriate formulation techniques (e.g., by presence of suitable solubilizing agents).

The non-toxic pharmaceutically acceptable inert diluent employed in the present invention can be selected from among any one of a number of diluents familiar to those skilled in the art. However, without limitation, the following are illustrative: lactose, starch (pharmaceutical grade), dicalcium phosphate, calcium sulfate, kaolin, mannitol and powdered sugar. Additionally, when required, suitable binders, lubricants and disintegrating agents can be added as well. Typical binders include starch, gelatin, sugars such as sucrose, molasses and lactose, natural and synthetic gums such as acacia, sodium alginate, extract of Irish Moss, carboxymethylcellulose, methylcellulose and polyvinylpyrrolidone, polyethylene glycol, ethylcellulose and waxes. Typical lubricants include, without limitation, boric acid, sodium benzoate, sodium acetate, sodium chloride, leucine and polyethylene glycol. Finally, suitable disintegrators can include, without limitation, starch, methylcellulose, agar, bentonite, cellulose and wood products, alginic acid, guar gum, citris pulp, carboxymethylcellulose and sodium lauryl sulfate.

The tablets of the present invention may be slightly more fragile than conventional tablet preparations from a tablet-strength standpoint, since the former contain an effervescent agent. For this reason, it may be especially desirable to incorporate therein a dry binding agent such as microcrystalline cellulose. In addition, the incorporation of microcrystalline cellulose may improve the immediate release of erythromycin at the optimum absorption site. Naturally, other binders, stabilizers, lubricants and disintegrators can be added as well.

As for the enteric coating material to be employed in the instant invention, any conventional enteric coating is suitable. For example, without limitation, cellulose acetate phthalate (CAP) and hydroxypropylmethylcellulose phthalate (HPMCP), etc., are suitable. Other enteric coatings suitable for the purpose of the instant invention can be found in the text entitled "Remington's Pharmaceutical Sciences," Fourteenth Edition (1970), pages 1689–1691. It is preferable to employ those enteric coatings which dissolve in a pH range of from 4.5 to 5.0 in order that the active ingredient can be released at the optimum absorption site in the small intestine. Illustrative but not limitative examples of such materials are HPMCP-50 and HPMCP-45.

As for the effervescing agent, naturally, a non-toxic pharmaceutically acceptable effervescent (i.e., carbon dioxide releasing) couple acid (e.g., tartaric acid, citric acid, citric anhydride and the like) and base (e.g., sodium bicarbonate, sodium carbonate, etc.) are required. Additional effervescent couple acids and bases can be found in "Remington's Pharmaceutical Sciences," Fourteenth Edition (1970), pages 802, 803 and 1462.

Upon contact of the effervescent enteric-coated preparation with the intestinal juice, effervescence rapidly occurs, thus causing total disintegration and release of the soluble form of erythromycin all at once.

Without further elaboration, it is believed that one of ordinary skill in the art can, using the preceding description, utilize the present invention to its fullest extent. As such, the following preferred specific embodiments are, therefore, to be construed as merely illustrative and not limitative of the remainder of the specification and claims in any way whatsoever.

EXAMPLE I

The following composition is formulated into an effervescent-enteric coated tablet weighing 364 mg per tablet.

| Ingredient | Amount |
| --- | --- |
| Erythromycin lactobionate | 200 mg |
| Tartaric acid | 50 mg |
| Sodium bicarbonate | 56 mg |
| Carboxymethylcellulose | 20 mg |
| Microcrystalline cellulose | 30 mg |
| Talc | 6 mg |
| Magnesium stearate | 2 mg |
| TOTAL | 364 mg |

Onto this tablet, there is sprayed a solution of 10% w/w (HPMCP-50) dissolved in a 1:1 (by weight) mixture of methylene chloride and ethanol. The tablet is coated until the total weight thereof increases by 10% w/w (based on the uncoated tablet). Thus is obtained the final product.

EXAMPLE II

The following composition is formulated into an effervescent coated tablet weighing 376 mg per tablet.

| Ingredient | Amount |
| --- | --- |
| Erythromycin glucoheptonate | 200 mg |
| Citric acid | 62 mg |
| Sodium bicarbonate | 56 mg |
| Carboxymethylcellulose | 20 mg |
| Microcrystalline cellulose | 30 mg |
| Talc | 6 mg |
| Magnesium stearate | 2 mg |
| TOTAL | 376 mg |

This tablet is coated in the same manner as the tablet of Example I to give the final effervescent-enteric coated product.

EXAMPLE III

A table prepared in the same manner as the tablet in Example I is sprayed with a solution of 8% (w/w) cellulose acetate phthalate and 2% (w/w) polyethylene glycol 6000 dissolved in acetone. The tablet is coated until the total weight thereof increases by 10% (w/w) based on the uncoated tablet.

From the foregoing description, one of ordinary skill in the art can easily ascertain the essential characteristics of the instant invention, and without departing from the spirit and scope thereof, can make various changes and modifications of the invention to adapt it to various usages and conditions. As such, these changes and modifications are properly, equitably, and intended to be, within the full range of equivalence of the following claims.

What I claim is:

1. A pharmaceutically acceptable effervescent enteric-coated tablet for orally delivering therapeutic levels of erythromycin to a warm-blooded animal, which comprises a tableted admixture of:
   (a) an antibiotic effective amount of a non-toxic pharmaceutically acceptable salt of erythromycin which is readily soluble in the intestines;
   (b) a non-toxic pharmaceutically acceptable inert diluent; and
   (c) a non-toxic pharmaceutically acceptable effervescent couple acid and base; and
   (d) a non-toxic pharmaceutically acceptable enteric coating maintained over the tableted admixture of (a), (b), and (c) above.

2. The tablet of claim 1, wherein said soluble salt of erythromycin is erythromycin lactobionate.

3. The tablet of claim 1, wherein said soluble salt of erythromycin is erythromycin glucoheptonate.

4. The tablet of claim 1, wherein said diluent is talc.

5. The tablet of claim 1, wherein said acid is a member selected from the group consisting of tartaric acid, citric acid, and phthalic acid.

6. The tablet of claim 1, wherein said base is sodium bicarbonate.

7. The tablet of claim 1, wherein said enteric coating is a member selected from the group consisting of cellulose acetate phthalate and hydroxypropylmethylcellulose phthalate.

8. The tablet of claim 7, wherein said hydroxypropylmethylcellulose phthalate is a member selected from the group consisting of hydroxypropylmethylcellulose phthalate-50 and hydroxypropylmethylcellulose phthalate-45.

9. The tablet of claim 1, further comprising microcrystalline cellulose as a dry binding agent.

10. A method for inducing therapeutic levels of erythromycin in a warm-blooded animal which comprises administering thereto a tablet as claimed in claim 1.

* * * * *